Figure 1:
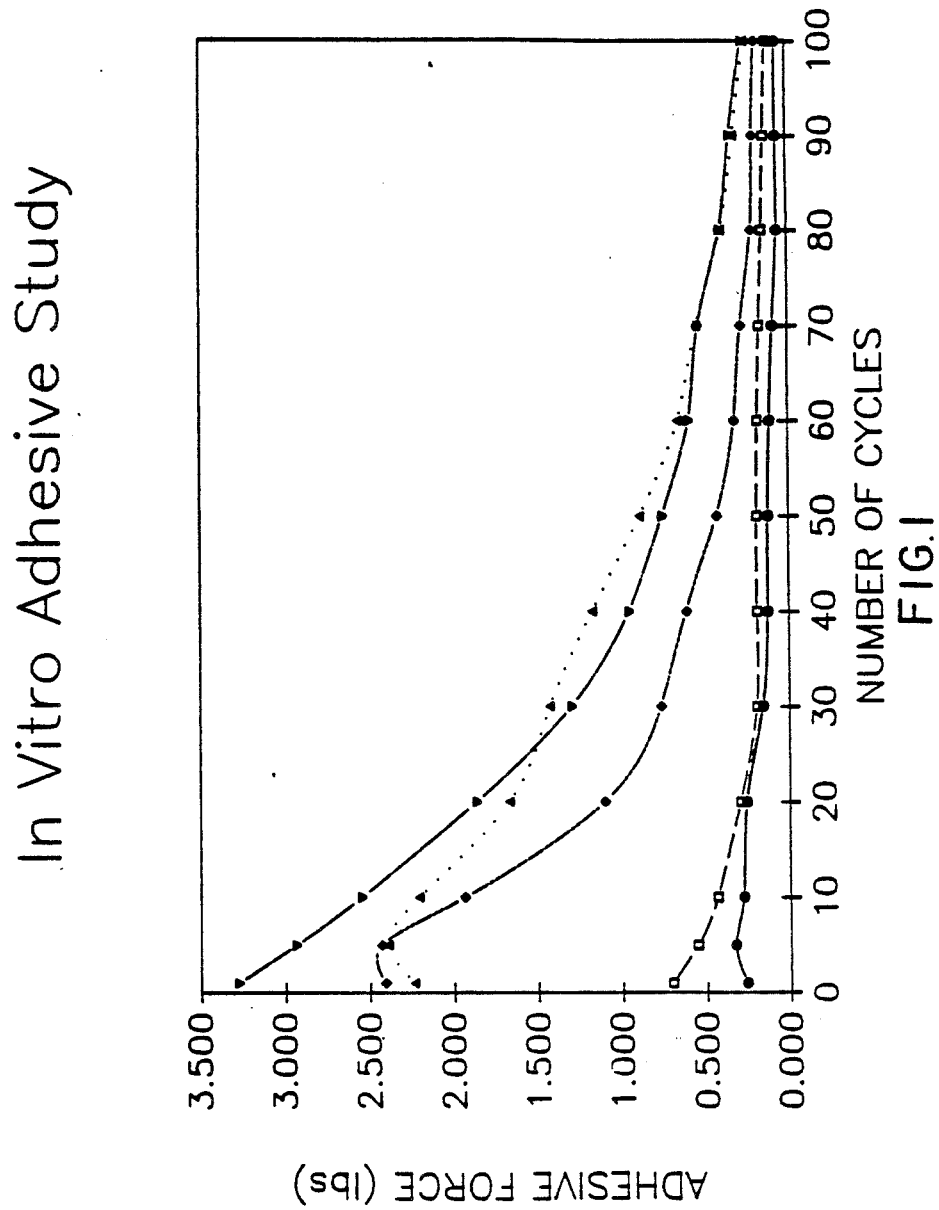
Figure 2:
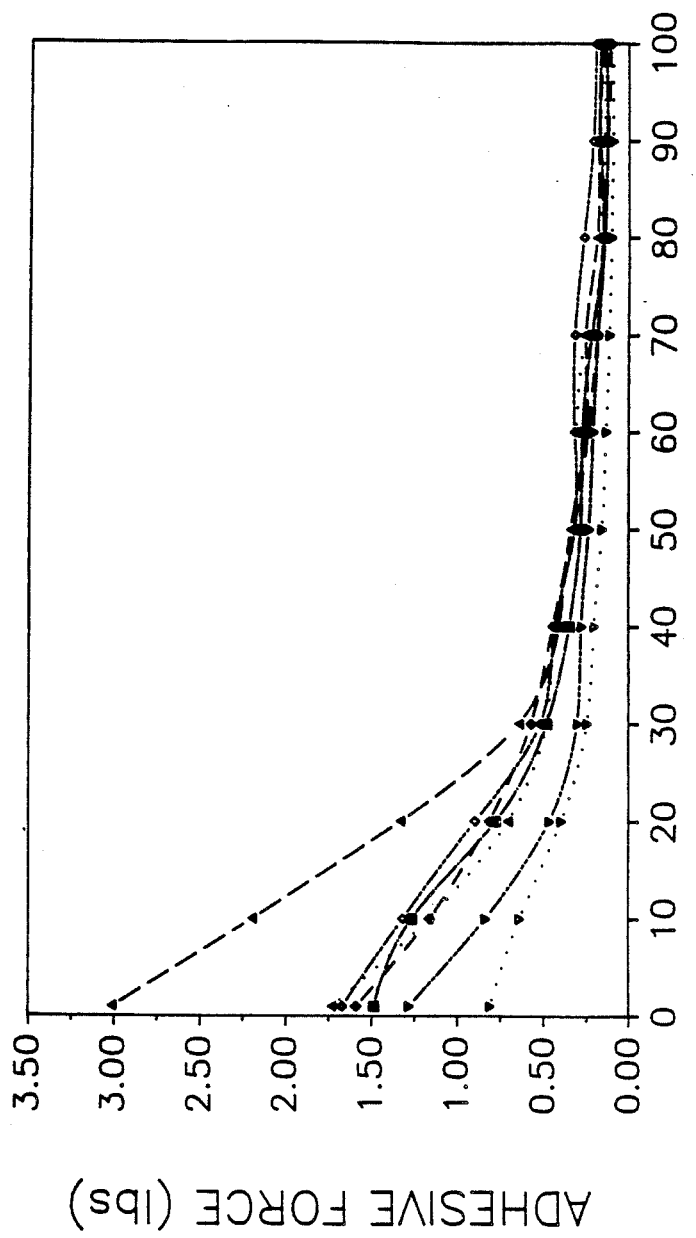

United States Patent [19]

Haldar et al.

[11] Patent Number: 4,910,247

[45] Date of Patent: Mar. 20, 1990

[54] ADHESIVE COMPOSITION

[75] Inventors: Rama K. Haldar, Randolph; Balgopal Gangadharan, Caldwell; Ratan K. Chaudhuri, Butler, all of N.J.

[73] Assignee: GAF Chemicals Corporation, Wayne, N.J.

[21] Appl. No.: 329,036

[22] Filed: Mar. 27, 1989

[51] Int. Cl.$^4$ ................................................ C08K 5/09
[52] U.S. Cl. .................................... 524/400; 523/118; 523/120; 523/121; 524/559
[58] Field of Search ....................... 523/118, 120, 121; 524/400, 559

[56] References Cited

U.S. PATENT DOCUMENTS

| | | | |
|---|---|---|---|
| 3,003,988 | 10/1961 | Germann et al. | 525/327.8 |
| 3,868,339 | 2/1975 | Keegan et al. | 523/120 |
| 4,393,080 | 7/1983 | Pawelchak et al. | 523/118 |
| 4,758,630 | 7/1988 | Shah et al. | 523/120 |

OTHER PUBLICATIONS

"Characteristics of Fine Particles", Chemical Engineering, Jun. 11, 1962, p. 207.
Rodriguez, Ferdinand, *Principles of Polymer Systems*, McGraw-Hill, New York, 1982, p. 142.

*Primary Examiner*—Joseph L. Schofer
*Assistant Examiner*—R. H. Delmendo
*Attorney, Agent, or Firm*—Marilyn J. Maue; Joshua J. Ward

[57] ABSTRACT

A composition containing an adhesive suitable for affixing dentures or ostomy devices to a mucous membrane, which adhesive is a mixture composed of (a) 75-25 wt. % of a blend comprising a divalent calcium salt and a monovalent sodium salt of a lower alkyl vinyl ether/maleic acid copolymer wherein the concentration of Ca is between about 10 and 15 wt. % of the blend; Na is between about 1.5 and about 4 wt. % of the blend and —COOH is between about 9 and about 25 wt. % of the blend;

(b) 0–10 wt. % of a lower alkyl vinyl ether/maleic acid auxiliary metal salt wherein said metal is divalent magnesium and/or monovalent potassium and wherein said auxiliary metal represents between about 1.5 and about 15 wt. % of said auxiliary metal salt compound and (c) 25–75 wt. % of a stearic acid metal salt wherein said metal salt is magnesium stearate containing from 0% to about 75% sodium stearate.

The invention also relates to the use of said composition as an adhesive used in association with mucous membranes.

16 Claims, 2 Drawing Sheets

ADHESIVE COMPOSITION

BACKGROUND OF THE INVENTION

Various adhesive compositions have been employed for fixing dentures or ostomy devices to mucous membranes, several of which involve the use of methyl vinyl ether-maleic acid metal salts as the active adhesive agent. U.S. patents disclosing such compositions include U.S. Pat. Nos. 3,003,988; 3,736,274; 3,833,518; 3,868,339; 4,758,630; 4,183,914; 4,217,342 and 4,217,343. Such denture adhesive compositions containing the above salts of methyl vinyl ether/maleic acid copolymers are found to be effective for a limited time of up to 8 hours and some for as little as 2 or 3 hours.

Accordingly, it is an object of this invention to provide an adhesive composition having improved strength and temperature stability and retaining its strong adhesive properties over substantially increased periods of time.

Another object is to provide an adhesive composition which contains a particular selection of adhesive ingredients which interact to afford a viscosity relatively independent of temperature changes within the range of from about 5° to about 50° C.

Still another object is to provide a composition which is economical and which can be readily processed in standard commercial blending equipment.

These and other objects of the invention will become apparent from the following description and disclosure.

THE INVENTION

According to this invention there is provided a composition containing an adhesive mixture suitable for affixing dentures or ostomy devices to membrane tissue, which adhesive is composed of (a) 75-25 wt. % of a blend comprising a divalent calcium salt and a monovalent sodium salt of a lower alkyl vinyl ether/maleic acid copolymer wherein the concentration of Ca is between about 10 and 15 wt. % of the blend; Na is between about 1.5 and about 4 wt. % of the blend and —COOH is between about 9 and about 25 wt. % of the blend;

(b) 0-10 wt. % of a lower alkyl vinyl ether/maleic acid auxiliary metal salt wherein said metal is divalent magnesium and/or monovalent potassium and wherein said auxiliary metal represents between about 1.5 and about 15 wt. % of said auxiliary metal salt compound and (c) 25-75 wt. % of a stearic acid metal salt wherein said metal salt is magnesium stearate containing from 0% to about 75% sodium stearate.

Of the stearate components employed in the present composition, the divalent magnesium stearate, i.e. $Mg[OOC-(CH_2)_{17}]_2$ is preferred over the mixture with more than 50% monovalent sodium stearate, i.e. $NaOOC-(CH_2)_{17}$. The copolymeric salt blend of component (a) is preferably one wherein Ca represents 11-13 wt. %; Na represents 2-2.5 wt. %; free acid represents between 15 and 20 wt. % of the blend; R is methyl and the adhesive mixture of (a), (c) and optionally (b) contains from 55-45 wt. % of component (a) and 45-55 wt. % of component (c) not more than 2 wt. % of the auxiliary metal salt copolymer.

In accordance with the above description the present adhesive agent contains a blend of a magnesium salt or magnesium and sodium salt mixture of stearic acid and a lower alkyl vinyl ether/maleic acid salt containing units of the formula

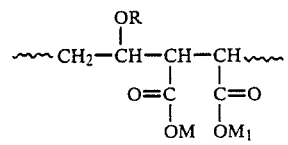

wherein both M and $M_1$ can be calcium; M or $M_1$ is sodium or calcium and the remaining M or $M_1$ is hydrogen, or mixtures thereof. The copolymeric salt can also be crosslinked with divalent calcium to provide a unit of the structure

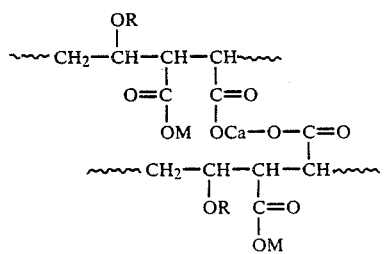

Similarly, an adhesive which includes an auxiliary salt polymer contains units of the formula

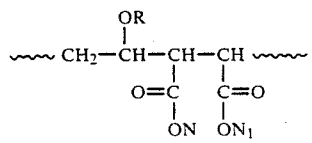

wherein both N and $N_1$ are magnesium, N or $N_1$ is potassium or magnesium and the remaining N or $N_1$ is hydrogen or a unit where the copolymer is crosslinked with divalent magnesium corresponding to formula B above, which may occur in admixture with the aforementioned units.

In general, the copolymers in the adhesive mixture have from about 40 to about 90%, preferably from about 70 to about 90%, of the initial carboxyl groups reacted with metal and are characterized as having a molecular weight of between about 18,000 and about 80,000, preferably between about 40,000 and about 60,000 as measured by membrane osmometry in 2-butanone 1-10 grams/1000 ml solution). The various metal salts of lower alkyl vinyl ether/maleic acid copolymers can be prepared by reacting the desired amount of metal hydroxide with a lower alkyl vinyl ether/maleic acid or maleic anhydride copolymer having a molecular weight of from about 18,000 to about 80,000. Such alkyl vinyl ether/maleic acid or anhydride copolymers are commercially available from GAF Corporation and sold as GANTREZ®, S series (MW ~ 18,000-70,000); MS series (MW ~ 60,000-75,000) and AN series (MW ~ 18,000-80,000). The resultant metal salt product in which a portion of the original carboxyl groups are neutralized, is then dried and milled to a suitable particle size. Alternatively, a commercially available calcium and sodium salt mixture of lower alkyl vinyl ether/maleic acid copolymer can be used in the present adhesive mixture. Such a polymeric salt blend is supplied by GAF Corporation as GANTREZ®, MS 955 wherein the proportion of Ca:Na is about 5-6:1 and the molecular weight is about 65,000-70,000.

The viscosity of the final adhesive composition with base carrier is stabilized to a viscosity of between about 2,000 cps and about 10,000 cps. The admixture without the base has a pH 5.5 to about 7 (2% solution in water at 25° C.).

The adhesive mixture of this invention is employed as a dry powder having a particle size less than 250μ, more desirably a particle size of from about 5 to about 200μ.

The above adhesive mixture is incorporated into a liquid base carrier as a powder by mixing until a homogeneous suspension or colloidal dispersion is obtained, usually within a period of from about 20 minutes to about 5 hours. The resulting composition contains an effective adhesive amount of the adhesive mixture, generally between about 5 and about 50 wt. %, preferably between about 10 and about 35 wt. %, of the final composition.

The present adhesive mixture can be employed as the sole adhesive component in the composition or it can be used as a coadhesive in joint usage with a minor proportion, e.g. 5-20% by weight, of another active material or synthetic adhesive component, if desired. Suitable adhesive additives include natural or synthetic polymers such as cellulose, karaya gum, gum tragacanth, gum acacia, carboxymethyl cellulose or salt thereof, polymethacrylate, polyvinylpyrrolidone, polyvinyl acetate, or any mixture of the above. The base carrie portion of the composition generally includes a water soluble or partially water soluble hydrophilic carrier which is capable of swelling upon exposure to moisture to form a mucilaginous mass. Such carrier materials include natural and synthetic gums, viscous liquids, gels and powders. Among those suitably employed as base carriers in the composition are Karaya gum, gelatine, gum tragacanth, gum acacia, gum shiraz, algin, sodium alginate, tragacanth, methyl cellulose, a mixture of petroleum and mineral oil, glycerine, polyvinyl- pyrrolidone, K-30 and K-90, carboxymethyl cellulose, ethylene oxide polymers, of which the preferred is a mixture of petrolatum and mineral oil in a ratio of 40:60-60:40. Auxiliary adhesives, when employed, are used in minor amount not exceeding 10%, desirably not exceeding 2%, of the adhesive mixture disclosed herein. Flavoring agents and coloring agents may also be included in the composition, if desired. Additionally, a small amount, 0.5-1%, of a quaternized N-propylamino loctam deodorizer can be included.

Alternatively, between about 5-10 wt. % of the present adhesive mixture can be incorporated as a dry powder composition with sodium perborate, a water soluble ethylene oxide polymer etc. in the above concentrations.

The present compositions are particularly useful for affixing dentures or ostomy devices and can also be used in surgical procedures which require temporary displacement of tissue. As a denture adhesive, the thermal stability of the present composition, over a temperature range which is at least sufficient to embrace all conditions encountered by living tissue, e.g. 5°-50° C., is particularly desirable. Another important property of the present composition is that of improved strength wherein the holding power is increased at least twofold, and in many cases four-fold, over copolymeric partial salts presently in use. Because of their increased adhesive strength and thermal stability, the composition retains its adhesive properties over a longer period of time, i.e. a period of up to 24 hours. Finally, the composition has high membrane substantivity and is non-toxic in all concentrations within the prescribed ranges.

The following illustrates a few representative formulations which the present composition can be added in amounts up to about 50%.

| | wt. % |
|---|---|
| Cream Denture Adhesive | |
| Mineral Oil | 30 |
| Petrolatum | 25 |
| Sodium carboxymethyl cellulose (adhesive additive) | 20 |
| Colorant | 1 |
| Flavoring Agent | 0.5 |
| Present composition | 23.5 |
| Paste Ostomy Adhesive | |
| Mineral oil (heavy) | 35 |
| Glycerine | 5 |
| Polyvinylpyrrolidone | 20 |
| Carboxymethyl cellulose | 5 |
| Tosylate of quat. amino-N-propylpyrrolidone | 0.5 |
| Present composition | 34.5 |
| Denture Adhesive Powder | |
| gum tragacanth | 40 |
| gum acacia | 20 |
| spearmint oil | 0.05 |
| Present composition | 39.05 |

Having thus generally described the adhesive compositions of the present invention, reference is now had to the following examples which provide preferred embodiments and present comparative data with other denture adhesives of the art. However, these examples are not to be construed as limiting to the scope of the invention as more broadly described above and in the appended claims.

EXAMPLE 1

Dry GANTREZ MS-955* and magnesium stearate were separately milled to pass through a number 60 mesh sieve (250μ) and the resulting powders, in a 50-50 gram mixture were combined and blended in a Patterson-Kelly V blender for 30 minutes at room temperature. The blended mixture was then dispersed in a petrolatum bath with a mechanical stirrer at a temperature of 55°-65° C. so as to provide a ratio of polymer to base of 1:2. The resulting cream dispersion was collected as the desired adhesive composition.

* a copolymeric methyl vinyl ether/maleic acid mixed salt of calcium and sodium having 80-90% of the carboxyl groups neutralized with calcium and sodium in a ratio of 5 or 6:1 Ca to Na; said polymer having an average molecular weight of about 67,000.

EXAMPLE 2

Example 1 was repeated except that a mixture of 25/75 GANTREZ/magnesium stearate was blended to provide the cream adhesive composition.

EXAMPLE 3

Example 1 was repeated except that the stearate salt was omitted. The product composition was a dispersion of GANTREZ MS-955 in petrolatum.

EXAMPLE 4

Example 1 was repeated except that the stearate salt was 25 g. of magnesium stearate and 25 g. of sodium stearate. The product composition was a dispersion of the components in petrolatum.

EXAMPLE 5

Example 1 was repeated except that sodium stearate was substituted for magnesium stearate. The product composition was a dispersion of these components in petrolatum.

EXAMPLE 6

2 gram samples of each of the compositions prepared in Examples 1-5 were evaluated for adhesion characteristics by Instron study according to the following procedure.

In the first step, the upper and lower plates of the Instron apparatus are brought together to obtain a zero position. The upper plate is then raised 0.06 inch and the upper cycle limit on the Instron indicator is set at this point. The upper plate is then lowered and the lower cycle limit is set. In its lowest position, the upper plate is distanced 0.03 inch above the lower plate.

With these Instron settings determined, the upper plate was then raised and 2 grams of the sample was uniformly spread over the surface of the lower plate in a 1/16 to ⅛ inch thickness; after which simulated salivary fluid was applied over the sample so that it was barely covered.

The Instron crosshead was cycled between the previously set limits at a crosshead speed of 0.2 in./min. The Instron chart was set in the continuous mode at a speed of 2 in./min. to record the compression and adhesion force for each cycle, 5 to 100 cycles.

At the end of 100 cycles, the motion of the upper plate was halted and raised high enough to clean the surface before the next adhesive test.

Each recording was analyzed and the adhesion forces (lbs.) for the 1st, 5th, 10th, 15th . . . 100th cycles were recorded and then plotted on a graph as shown in FIG. I.

In FIG. I, the results of testing the composition of Examples 1-5 are shown by the following cure indicators:

| Example 1 | △ |
| Example 2 | ▲ |
| Example 3 | ● |
| Example 4 | ◆ |
| Example 5 | □ |

The initial high adhesive force up to 50 cycles (equivalent to 5-6 hours use in vivo) is due to the hydration of the polymer. However, as increasing amounts of the simulated saliva penetrates the formulation, the composition softens and some portions become detached from the lower plate. Hence, there is observed a drop in adhesive force since a reduced amount of the formulation is available for evaluation.

EXAMPLE 7

Example 1 was repeated except that aluminum stearate was employed in place of magnesium stearate. The final composition was a cream dispersion of the components.

EXAMPLE 8

Example 1 was repeated except that barium stearate was employed in place of magnesium stearate. The final composition as a creme dispersion of the components.

EXAMPLE 9

Example 1 was repeated except that lithium stearate was employed in place of magnesium stearate. The final composition was a creme dispersion of the components.

EXAMPLE 10

Example 1 was repeated except that potassium stearate was employed in place of magnesium stearate. The final composition was a creme dispersion of the components.

EXAMPLE 11

Example 1 was repeated except that strontium stearate was employed in place of magnesium stearate. The final composition was a creme dispersion of the components.

EXAMPLE 12

Example 1 was repeated except that calcium stearate was employed in place of magnesium stearate. The final composition was a creme dispersion of the components.

EXAMPLE 13

Example 1 was repeated except that zinc stearate was employed in place of magnesium stearate. The final composition was a creme dispersion of the components.

EXAMPLE 14

Example 1 was repeated except that magnesium palmitate was employed in place of magnesium stearate. The final composition wa a creme dispersion of the components.

EXAMPLE 15

Example 1 was repeated except that magnesium behenate was employed in place of magnesium stearate. The final composition was a creme dispersion of the components.

EXAMPLE 16

Example 1 was repeated except that magnesium dodecanate was employed in place of magnesium stearate. The final composition was a creme dispersion of the components.

EXAMPLE 17

Example 1 was repeated except that the following components were used. The final composition was a creme dispersion of the components.

| Components | % W/W |
| --- | --- |
| Gantrez MS 955 + Magnesium stearate (50:50) | 30 |
| Carboxymethyl Cellulose | 15 |
| Mineral oil | 25 |
| White Petrolatum | 24 |
| Others (color, flavor, sweetner) | 6 |

EXAMPLE 18

Example 1 was repeated except that the following components were used. The final composition was a creme dispersion of the components.

| Components | % W/W |
| --- | --- |
| Gantrez MS 955 + Magnesium stearate (50:50) | 35 |
| Karaya gum | 10 |
| Mineral oil | 20 |
| White Petrolatum | 29 |
| Others (color, flavor, sweetner) | 6 |

EXAMPLE 19

2 gram samples of each of the compositions prepared in Examples 7–13 were evaluated for adhesion characteristics by the Instron procedure set forth in Example 6. Similarly, the recordings were analyzed and the adhesional forces (lbs.) were recorded and plotted on a graph as shown in FIG. II.

In FIG. II, the results of testing the compositions of Examples 7–13 are shown by the following curve indicators.

| | |
| --- | --- |
| Example 7 | ▲ |
| Example 8 | △ |
| Example 9 | ■ |
| Example 10 | ▼ |
| Example 11 | ▽ |
| Example 12 | ◆ |
| Example 13 | ◇ |

What is claimed is:

1. A creme or paste adhesive composition containing an adhesive mixture comprising
   (a) 75–25 wt. % of a blend comprising a divalent calcium salt and a monovalent sodium salt of a lower alkyl vinyl ether/maleic acid copolymer wherein the concentration of Ca is between about 10 and 15 wt. % of the blend; Na is between about 1.5 and about 4 wt % of the blend and —COOH is between about 9 and about 25 wt. % of the blend;
   (b) 0–10 wt. % of a lower alkyl vinyl ether/maleic acid auxiliary metal salt wherein said metal is divalent magnesium and/or monovalent potassium and wherein said auxiliary metal represents between about 1.5 and about 15 wt. % of said auxiliary metal salt compound and
   (c) 25–75 wt. % of a stearic acid metal salt wherein said metal salt is magnesium stearate containing from 0% to about 75% sodium stearate.

2. The composition of claim 1 wherein the lower alkyl vinyl ether is methyl vinyl ether.

3. The composition of claim 1 wherein the adhesive mixture contains from about 55 to about 45 wt. % of component (a) from about 45 to about 55 wt. % of component (c) and not more than 2 wt. % of component (b).

4. The composition of claim 3 in which component (b) is zero.

5. The composition of claim 1 wherein the copolymeric salt blend of component (a) has 11–13 wt. % Ca; 2.–2.5 wt. % Na and 15–20 wt. % free acid.

6. The composition of claim 2 wherein the methyl vinyl ether/maleic acid copolymer salt has a molecular weight of from about 30,000 to about 80,000 and a particle size less than 250 μ.

7. The composition of claim 6 wherein said molecular weight is between about 40,000 and about 60,000 and a particle size less than 200 μ.

8. The composition of claim 1 wherein the lower alkyl vinyl ether/maleic acid copolymer has between about 10% and about 60% of the carboxyl groups neutralized.

9. The composition of claim 2 wherein the methyl vinyl ether/maleic acid copolymer has between about 40% and about 50% of the carboxyl groups reacted with calcium an sodium.

10. The composition containing an effective adhesive producing amount of the adhesive mixture of claim 1 and a base carrier.

11. The composition of claim 10 wherein the adhesive mixture of claim 1 is present in a concentration of between about 5 and about 50 wt. %.

12. The composition of claim 1 additionally containing a minor amount of natural gum adhesive.

13. The composition of claim 12 wherein said natural gum is karaya gum.

14. The composition of claim 1 containing between about 5 and about 15 wt. % of an adhesive polymer additive.

15. The composition of claim 14 wherein said adhesive polymer additive is carboxymethyl cellulose.

16. The composition of claim 14 wherein said adhesive polymer additive is a synthetic polymer.

* * * * *